United States Patent [19]

Sutherland et al.

[11] Patent Number: 5,049,490

[45] Date of Patent: Sep. 17, 1991

[54] QUANTITATIVE DETERMINATION OF A DNA POLYMERASE AND A TEST KIT USEFUL IN SAME

[75] Inventors: John W. H. Sutherland, Rochester, N.Y.; Patrick J. Sheridan, San Leandro; Louis M. Mezei, Fremont, both of Calif.

[73] Assignees: Eastman Kodak Co., Rochester, N.Y.; Cetus Corporation, Emeryville, Calif.

[21] Appl. No.: 482,137

[22] Filed: Feb. 20, 1990

[51] Int. Cl.⁵ .................... C12Q 1/68; C07H 15/12; C12N 15/00
[52] U.S. Cl. ........................ 435/6; 536/27; 935/77; 935/78
[58] Field of Search ............... 435/6; 536/27; 935/77, 935/78

[56] References Cited

U.S. PATENT DOCUMENTS 4,683,195  7/1987  Mullis et al. .................... 435/6
4,683,202  7/1987  Mullis .............................. 435/91

FOREIGN PATENT DOCUMENTS 258017  8/1987  European Pat. Off. .

OTHER PUBLICATIONS

Labarca et al., *Anal. Biochem.*, 102, pp. 344–352 (1980).
Downs et al., *Anal. Biochem.*, 131, pp. 538–547 (1983).
Sterzel et al., *Anal. Biochem.*, 147, pp. 462–467 (1985).
Perkin Elmer Technical Bulletin L-913A, pp. 1–4 (Sep. 1983).
"Amplifications", Perkin Elmer Cetus Bulletin, pp. 8–10 (Feb. 1989).
West et al., *Anal. Biochem.*, 147, pp. 289–295 (1985).
Cesavone et al., *Anal. Biochem.*, 100, pp. 188–197 (1979).
Stout et al., *Anal. Biochem.*, 127, pp. 302–307 (1982).

*Primary Examiner*—Robert A. Wax
*Assistant Examiner*—Mindy B. Fleisher
*Attorney, Agent, or Firm*—J. Lanny Tucker

[57] ABSTRACT

A convenient method for the quantitative determination of a DNA polymerase includes contacting an aqueous test specimen suspected of containing the enzyme with the following: a single-stranded DNA template present in a concentration of at least about $10^{-8}$ molar bases, a DNA primer complementary to the template, a source of a metal polymerase cofactor, sufficient deoxyribonucleoside triphosphates to synthesize double-stranded DNA in the presence of the polymerase, and a colorimetric or fluorescent dye which is capable of providing a detectable signal when a primed single-stranded nucleic acid is converted to double-stranded DNA by the polymerase. The rate of signal generation is then measured and can be correlated with the level of DNA polymerase in the specimen using graphical or mathematical means. The results of this method are precise, having a covariance of less than about 10%. A test kit includes the reagents needed for carrying out this method.

22 Claims, 11 Drawing Sheets

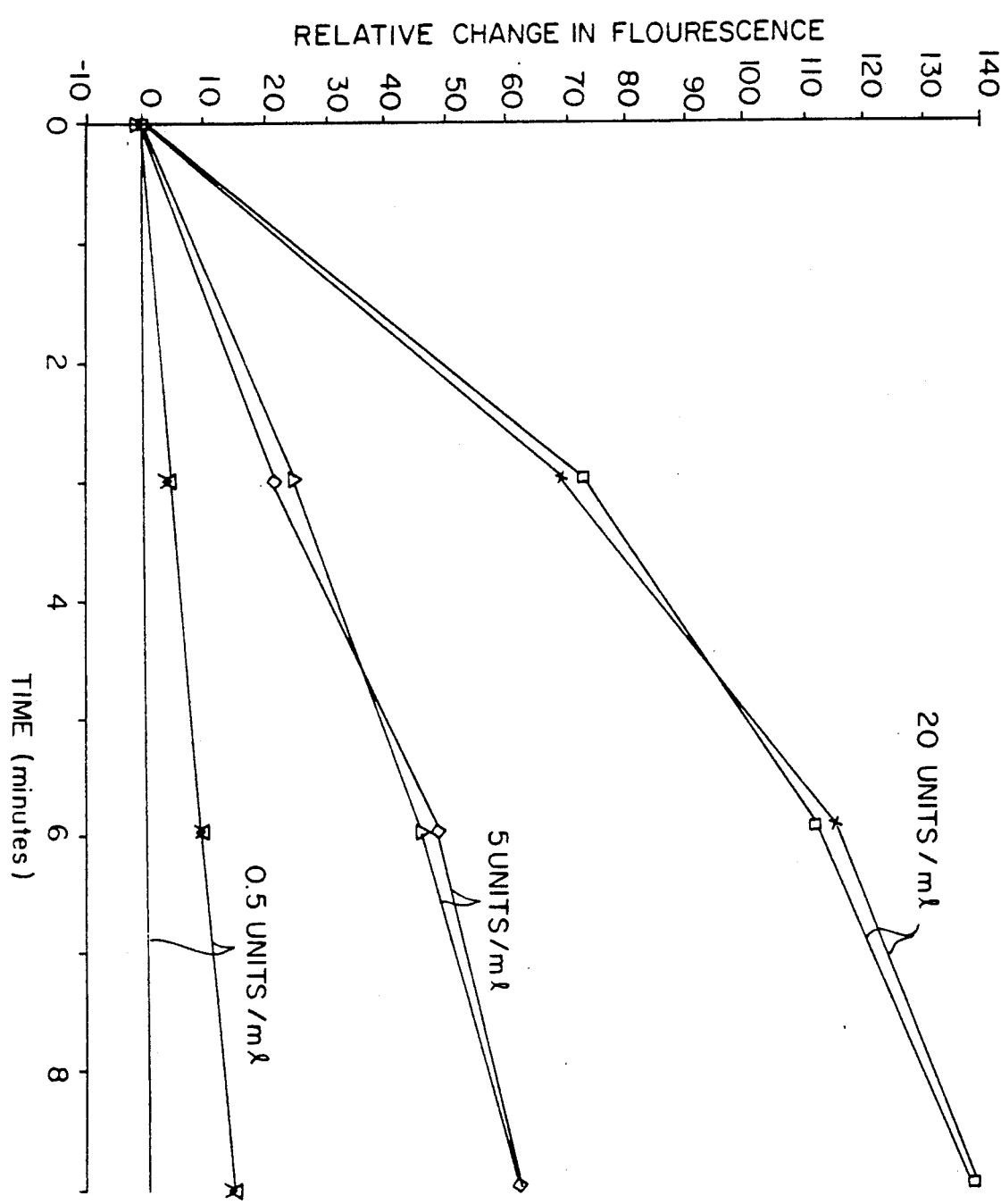

QUANTITATIVE DETERMINATION OF A DNA POLYMERASE AND A TEST KIT USEFUL IN SAME

FIELD OF THE INVENTION

This invention relates to a method for the quantitation of a DNA polymerase in an aqueous specimen, such as a reaction, cloning or culturing medium or diagnostic specimen. It also relates to a test kit containing reagents for carrying out this method.

BACKGROUND OF THE INVENTION

Within the field of biological diagnostics, more research and analytical procedures require the investigation of nucleic acids from biological specimens, such as whole blood, serum, semen, biological tissues and other human or animal sources. For diagnostic applications in particular, a targeted nucleic acid sequence may be only a small portion of the DNA or RNA being considered, so that detection of its presence may be very difficult. The well known DNA probe technology is steadily being improved to address this problem, providing more sensitive probes.

However, a significant development in providing highly detectable quantities of nucleic acids is described in U.S. Pat. No. 4,683,195 (issued July 28, 1987 to Mullis et al) and U.S. Pat. No. 4,683,202 (issued July 28, 1987 to Mullis). These references describe the amplification of a targeted nucleic acid sequence using DNA primers and agents for adding bases to DNA strands complementary to the targeted sequence. After a multiplicity of cycles of priming, extending DNA strands and denaturation, the targeted nucleic acid can be more readily detected using labeled primers, probes or other means.

Primer extension is accomplished in the presence of suitable amounts of deoxyribonucleoside triphosphates and an agent for inducing the extension (also called a polymerization agent). Generally, such agent is a DNA polymerase such as an *E. coli* DNA polymerase I, Klenow polymerase, T4 DNA polymerase and others which will facilitate combination of the deoxyribonucleoside triphosphates in the proper manner to form the primer extension products. Particularly useful enzymes are thermally stable enzymes, cloned or naturally occurring, such as those obtained from various bacterial species, such as the Thermus species. Some useful polymerases are commercially available. Generally, the synthesis of extension products will be initiated at the 3' end of each primer and proceed in the 5' to 3' direction along the template until synthesis is terminated.

Preferred thermally stable enzymes are DNA polymerases from *Thermus aquaticus*, such as described in EP-A-0 258 017 (published Mar. 2, 1988).

In various instances, it is important to know how much DNA polymerase is present in a medium. It is quite costly to isolate or clone a polymerase, and its efficient use is highly desirable. The amount of polymerase present in a sequencing process should be determinable. In the isolation or cloning of polymerases, it would be desirable to know when the desired concentration of enzyme has been obtained. In addition, it may be necessary to understand the enzymatic capabilities of a given polymerase in a given amplification medium.

Various isolation and purification methods for DNA polymerases are known in the art (including those references noted above). EP-A-0 258 017 (noted above) mentions a number of them. The thermostable enzymes described in that reference are assayed using a tedious six-step procedure described by Kaledin et al, *Biokhymiya*, 45, pp. 644–651 (1980) involving chromatography, fractionations and other time-consuming techniques.

Another procedure for measuring the amount of a DNA polymerase involves measuring the rate of incorporation of radioactively labeled deoxyribonucleoside triphosphates into a primer extension product (see generally Kornberg, *DNA Replication*, W. H. Freeman & Co., San Francisco, 1980, Chapters 4–6). However, this procedure likewise has a number of disadvantages, including imprecision and awkwardness. Moreover, the use of radioactive labels is not desired due to the handling and safety hazards involved.

It has been known for some time that certain fluorescent compounds (such as one known in the art as Hoechst 33258 Dye) bind preferentially to double-stranded DNA with a shift in signal as opposed to binding with the single-stranded form. See, for example, Labarca et al, *Anal. Biochem.*, 102, pp. 344–352 (1980), Downs et al, *Anal. Biochem.*, 131, pp. 538–547 (1983), Sterzel et al, *Anal. Biochem.*, 147, pp. 462–467 (1985), Perkin Elmer Technical Bulletin L-913A, Sept., 1986 and Perkin Elmer Cetus bulletin "Amplifications", pp. 8–10, February, 1989. Moreover, some researchers have used the Hoechst 33259 Dye in temperature optimization studies involving polymerase chain reaction. Such studies involved measuring the fluorescent signal obtained at certain time intervals for several polymerization temperatures. However, such studies were not used for, and indeed were incapable of, quantitatively determining the amount of polymerase in a specimen. In such instances, the rate of polymerase reaction was not measurable with accuracy, nor was a correlation established between the measured rate and polymerase activity.

Thus, while many researchers have considered the use of various dyes for detection of DNA, none of them suggests how they can be used to quantitatively determine the amount of a DNA polymerase in a solution. Yet, there is a need in the art for a quantitative, safe and convenient method for assaying for DNA polymerase in an aqueous medium.

SUMMARY OF THE INVENTION

The problems described above for known procedures are overcome using a method for the quantitative determination of a DNA polymerase, or a clone from a genome thereof, comprising:

A. bringing into contact:
   an aqueous test specimen believed to contain a DNA polymerase having activity $A_x$,
   a single-stranded DNA template which is present in a concentration of at least about $10^{-8}$ molar nucleotides,
   a DNA primer complementary to the template,
   a polymerase metal ion cofactor,
   sufficient deoxyribonucleoside triphosphates to generate a double-stranded DNA molecule from the template in the presence of the polymerase, and
   a colorimetric or fluorescent dye which, when bound to the double-stranded DNA formed from the template, exhibits a detectable signal as opposed to when the dye is bound to the template, and B. determining, with a precision having a covariance of less than about 10%, the activity $A_x$ of the polymerase in the test specimen corresponding to the rate of colorimetric or fluorometric signal generated by the binding of the dye to the double-stranded DNA formed by the action of the test specimen polymerase, the polymerase activity $A_x$ being determined as follows:

1) generating polymerase rates of reaction from the colorimetric or fluorometric signals generated over time by each of a series of samples containing DNA polymerase having known polymerase activities, $A_1, A_2, \ldots A_i \ldots A_n$ wherein n is the number of samples evaluated and is at least two, and generating the polymerase rate of reaction from the colorimetric or fluorometric signal generated over time from the test specimen,
2) determining a calibration using the rates of step 1) and the known polymerase activities $A_i$, and
3) predicting $A_x$ using the calibration of step 2) and the polymerase reaction rate of the test specimen.

Moreover, this invention also provides a test kit useful for the quantitative determination of a DNA polymerase, or a clone from a genome thereof, comprising:
a. a single-stranded phage DNA as a template,
b. the four deoxyribonucleoside triphosphates, dATP, dCTP, dGTP and dTTP,
c. a source of a metal ion DNA polymerase cofactor,
d. a DNA primer complementary to the DNA template suitable for forming a double-stranded DNA therefrom, and
e. a colorimetric or fluorescent dye which, when bound to the double-stranded DNA molecule formed from the template, exhibits a detectable signal as opposed to when the dye is bound to the template.

The present invention provides a rapid, quantitative and relatively simple means for measuring the amount of DNA polymerase in a speciment such as an extraction, sequencing or culture medium or other aqueous specimen suspected or known to contain a DNA polymerase. This analytical tool is also very useful in research and development studies of DNA polymerases where there is an interest in finding enzymes having improved polymerization efficiencies or thermostability. Moreover, the method can be used to study various parameters and reagents which are used in polymerase chain reactions. The incorporation of radioisotopes in order to determine the level of DNA polymerase activity, and the tedious, complicated analytical methods previously known, are avoided with the present invention. Further, unlike previous analytical attempts, this invention is highly quantitative and convenient.

The advantages of this invention are achieved by using certain dyes which exhibit a measurable difference in signal when bound to a double-stranded DNA molecule, as opposed to when they are bound to the corresponding single-stranded template. We have found a number of dyes which exhibit such changes. These changes can be used to monitor the rate of generation of double-stranded DNA from the corresponding single-stranded template, and accordingly quantitation of DNA polymerase activity. The rate of change of signal resulting from dye binding to double-stranded molecules is correlated to polymerase concentration quantitatively using a series of graphical or analytical steps, or combinations thereof, which are described in detail below. Such steps have not heretofore been used in combination with the dyes described herein for quantitative DNA polymerase determinations.

BRIEF DESCRIPTION OF THE DRAWINGS

FIG. 1A is a graphical plot of relative change in fluorescence versus time at three different concentrations of DNA polymerase. These data are described in more detail in Example 1 below.

DETAILED DESCRIPTION OF THE INVENTION

Figure 1B:
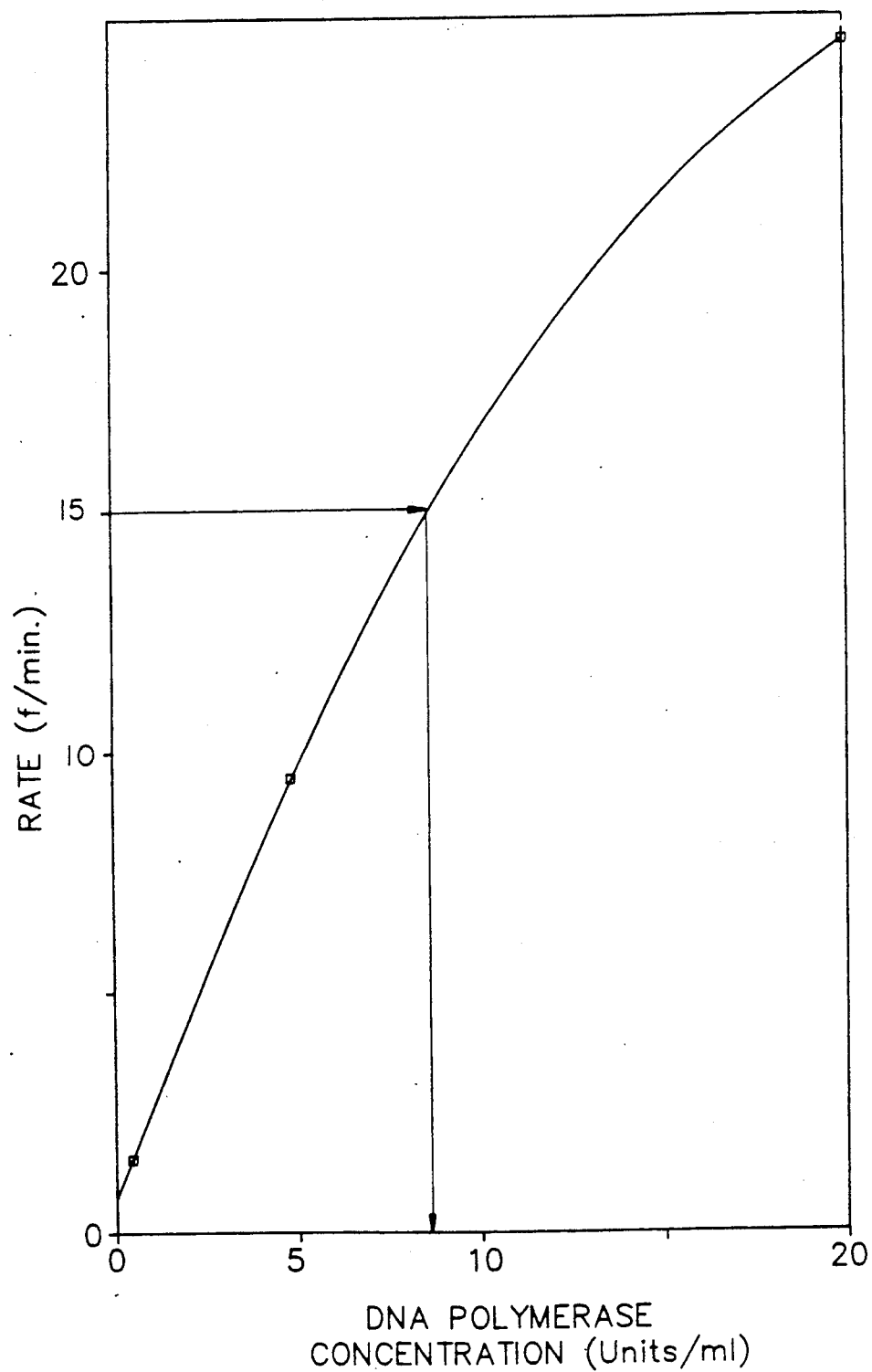
FIG. 1B is a graphical plot of rate of change in fluorescence over time versus DNA polymerase concentration (units/ml). These data are described in more detail in Example 1 below.

As noted above, there are instances where it is desired to measure the amount of a DNA polymerase in an aqueous medium. Known procedures are complex and tedious, and the present invention is much easier and convenient. The present invention can be used during procedures for isolation or cloning of DNA polymerases, during DNA sequencing procedures, research studies of various reaction parameters and reagents in polymerase chain reaction, as well as quality control procedures and other tests used in the manufacture of in vitro diagnostic test kits. Thus, the present invention can be used: (1) in the assay of specimen samples in which the amount of DNA polymerase is already known, but which is to be monitored in the study of other parameters, (2) in the assay of specimen samples wherein the presence of DNA polymerase is unknown, and (3) in the assay of specimen samples which are known to contain a DNA polymerase, but its concentration is unknown.

The DNA polymerases detectable by the present invention include enzymes which are naturally occurring or clones prepared from the appropriate genome using standard genetic engineering techniques. Many such enzymes are described in the art, and include, but are not limited to E. coli DNA polymerase I, T4 DNA polymerase, the Klenow subfragment and other fragments of other polymerases. The invention is particularly useful to detect thermally stable enzymes, cloned or naturally occurring, fragments or full-length molecules, such as those obtained from various Thermus bacterial species. Examples of preferred thermally stable enzymes detectable with this invention are DNA polymerases isolated from *Thermus aquaticus* such as those described in EP-A-0 258 017 (noted above). Other polymerases are described by Rossi et al, Syst. Appl. Microbiol. 7(2-3), pp. 337-341, 1986.

As used herein, the terms "single-stranded DNA" and "double-stranded DNA" refer to the entire DNA double helix molecule as well as a denatured single strand thereof, and to fragments of either the single-stranded or double-stranded molecule. In other words, an oligonucleotide alone or hybridized with a complementary oligonucleotide (of the same or different length) is included in the definition of these terms. When referring to a "template", what is meant is a single-stranded DNA which will become double-stranded DNA upon action by a DNA polymerase in the presence of the appropriate deoxyribonucleosides and suitable polymerization conditions.

In practicing the present invention, the aqueous test specimen having a polymerase which may contain one or more DNA polymerases of activity ($A_x$) is brought into contact with a number of materials which promote the formation of double-stranded DNA molecules from the single-stranded DNA template. These materials include the template (described below), a DNA primer substantially complementary to at least one sequence of the template, a polymerase metal cofactor which enhances polymerase activity and sufficient deoxyribonucleoside triphosphates which can be added to the template by the primer in forming the complementary strand.

The DNA template is a single-stranded oligonucleotide which is sufficiently long for a DNA primer to hybridize thereto and form a double-stranded DNA molecule to which the dye (defined below) can associate. Generally, the template is present in the reaction mixture in a concentration of at least about $10^{-8}$ molar nucleotides, and preferably from about $10^{-5}$ to about $10^{-3}$ molar nucleotides. Another way of stating this is that the template should be present at a concentration, depending upon its base length, that would allow sensitive detection in the method using the colorimetric or fluorometric dye. For shorter molecules, such as down to as low as 100-mer, the number of molecules present must be larger relative to the concentration of a 5000-mer DNA molecule. Thus, the molecular concentration would vary depending upon the length of the template. In most instances, this means the template has at least 100 nucleotides, and more likely from about 1000 to about 10,000 nucleotides. Preferably, the template has from about 5000 to about 8000 nucleotides. The template can be synthetic or naturally occurring, and some can be obtained commercially from a number of sources.

Various single-stranded phage DNA molecules can be used as templates, and a number of them are available commercially. A particularly useful template is M 13 phage DNA which is available commercially. Its use is advantageous because it is readily available in quantities needed for the assay, and in general, the initial polymerase activity using it is the maximum rate of polymerase activity. This provides a linear correlation of rate of signal change and polymerase activity, and hence polymerase concentration. Thus, this template provides a highly sensitive assay as well as a quantitative one.

As used herein, primers are oligonucleotides comprising ten or more deoxyribonucleotides. The exact size is not critical but depends upon many physical and chemical factors including the hybridization temperature and the degree of complementarity with the DNA template. The oligonucleotide is generally obtained synthetically.

The primer is capable of acting as a point of initiation of synthesis of connected nucleotides when placed under conditions in which synthesis of a primer extension product complementary to the DNA template is induced. Such conditions include the presence of suitable concentrations of the four standard deoxyribonucleoside triphosphates, an appropriate cofactor, the DNA polymerase, and suitable temperature and pH conditions.

The primer is substantially complementary to the DNA template. By "substantially complementary" is meant that there are a sufficient number of bases on the primer that match with the corresponding bases of the template that the primer will hybridize with that sequence. It does not mean, however, that every base pair must match. If there is a mismatch in the sequence, and particularly at the 3' end, various means can be used to overcome the mismatch, including the use of primer having thymine at the 3' end, as described in copending U.S. Ser. No. 406,221 (filed on Sept. 12, 1989 by Findlay et al and entitled "Diagnostic and Amplification Methods Overcoming a Primer-Target Mismatch at the Primer 3' End").

In the practice of this invention, generally the primers are entirely single-stranded. But there are primers known in the art which have a single-stranded region which is adjacent to a double-stranded region. Such primers can also be used if desired. The exact size of the primer will vary depending the length and complexity of the DNA template, reaction temperature and the source of the primer. Generally, the primers used in this invention will have from 10 to 50 nucleotides, and preferably, they have from 15 to 30 nucleotides. The amount of primer used will vary depending upon the template concentration, the amount of polymerase suspected, its likely activity and the length of time the assay is to be run. Generally, one or more primers are present in an amount of at least about $10^{-6}$ molar.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use. Naturally occurring primers isolated from biological sources are also useful (such as restriction endonuclease digests).

The formation of a primer extension product will occur with some DNA polymerases in the presence of the primer, DNA template and deoxyribonucleoside triphosphates (that is, dATP, dCTP, dGTP and dTTP) without cofactors present, but efficient polymerase activity for most enzymes generally requires the presence of a metal cofactor, such as a source of magnesium or manganese ion in amounts which are known in the art (generally, in molar excess of the triphosphates, for example at least about 1 mmolar). Magnesium ion is preferred.

Each of the deoxyribonucleoside triphosphates noted above are generally present in an amount of at least about 0.1 mmolar, and preferably from about 0.2 to about 2 mmolar.

The aqueous test specimen suspected of containing a predetermined (or targeted) polymerase is mixed with the noted materials in a medium which is generally buffered at a pH of from about 7 to about 9. Preferably, a molar excess of the primers is added to the buffered solution, and specific amounts are taught in the art. The deoxyribonucleoside triphosphates are also added in adequate amounts and the resulting solution is heated to about 30°–98° C. for up to about 30 minutes, and preferably from about 1 to about 15 minutes to form the extension product.

The test specimen, colorimetric or fluorometric dye and other reagents needed for the assay can be contacted in a number of ways and in various sequences. For example, the test specimen and dye can be mixed prior to contact with the other reagents. Alternatively, the colorimetric or fluorescent dye (defined below) can be mixed with the reagents prior to or simultaneously with the mixing of the reagents with the test specimen. The dye can be added all at once, or added in portions over a time period. There may be some advantages in sensitivity achieved by mixing test specimen and dye prior to contact with the other reagents. Preferably, the dye is mixed with aliquots of a reaction solution comprising the test specimen and the other reagents, selected at various time intervals during conversion of the template to double-stranded DNA, that is, after the extension reaction has been initiated.

Once all reagents (including the dye) have been mixed with the test specimen, the resulting detectable change in signal from dye binding to double-stranded DNA is monitored. Because the signal changes as the result of enzymatic reaction, the rate of change in signal is monitored. Thus, the signal can be an increase or decrease in fluorescence from a fluorescent dye, or it can be the shifting of the $\lambda_{max}$ of a colorimetric dye. With respect to colorimetric dyes, the shift in $\lambda_{max}$ can be from a colorless species (outside the visible region) to a colored species (within the visible region), from a colored species to a colorless species, or from one hue to another hue in the visible region of the electromagnetic spectrum. The rate of the measured change, or lack thereof, is then a measure of the activity of polymerase in the test specimen. The correlation of rate of change of the measured signal and the polymerase activity is described in more detail below. As one skilled in the art would readily understand, this invention could measure the activity of a mixture of polymerases in the specimen, but the individual activities of the polymerases would not be detectable.

Suitable equipment exists for measuring the change in detectable signal, including fluorometers and spectrophotometers. Suitable equipment for fluorescence measurements are available commercially as LS-2B or LS-5B fluorometers from Perkin Elmer.

Dyes which can be used in the practice of this invention are grouped as either colorimetric dyes (those providing a signal in the visible region of the spectrum), or fluorescent dyes (which are excited at one wavelength, and detected at an emission wavelength).

Preferably, the assay of this invention is carried out using fluorescent dyes, including but not limited to, bibenzimidazole, ethidium, methidium and acridine dyes. The bibenzimidazole dyes are preferred. Useful fluorescent dyes are selected from the group consisting of 2-[2-(4-hydroxyphenyl)-6-benzimidazole]-6-(1-methyl-4-piperazyl)benzimidazole trihydrochloride, acridine orange, methidium bromide, propidium bromide, ethidium bromide and 4',6'-diamindino-2-phenylindole. The first dye in this list is most preferred as it exhibits about a 50 nm shift upon binding to double-stranded DNA.

The amount of dye used in the assay will vary depending on the type and strength of signal it will provide when binding to DNA, and other factors known to one skilled in the art. Generally, it is present in an amount of at least about 1, and preferably from about 2 to about 5, $\mu$molar.

The assay can be carried out using all of the necessary reagents and materials obtained from separate sources, but advantageously, they are supplied as part of a diagnostic test kit. The critical components of such a kit include a suitable dye, a single-stranded phage DNA template (preferably, M 13 phage DNA), a polymerase metal cofactor, a DNA primer complementary to the template and the four deoxyribonucleoside triphosphates. Other materials, such as buffers, containers and instructions can also be included in the kit. The materials can be appropriately packaged (dry or wet) for needed stability, safety and ease of handling.

Polymerase activity ($A_x$) is determined with the present invention with a precision having a covariance of less than about 10%. Precision is a known statistical parameter in diagnositic and clinical assays for measuring reproducibility. Covariance is commonly defined as equal to the standard deviation ($\sigma$) for a number of replicate measurements divided by the mean x, the result then multiplied by 100%. The smaller the covariance, the more precise the assay, indicating the highly quantitative nature of the assay.

DESCRIPTION OF PREFERRED EMBODIMENTS

The method of this invention can be carried out using a number of graphical or mathematical functions which correlate the detectable signals obtained in the reaction to the activity of any DNA polymerase present in the test specimen. If no signals can be detectable, no polymerase is present. Generally, however, a test specimen is believed to have at least some polymerase present. While one skilled in the art would be able to use the teaching herein to find a number of ways to carry out the quantitative determination, we have considered four specific embodiments which are outlined as follows:

EMBODIMENT A

In this embodiment, determination of $A_x$ in step B of the method is carried out as follows:

step B1) is carried out by
  (a) generating curves from the colorimetric or fluorometric signals with time for each of the known polymerase activities, and generating a similar curve for the polymerase activity of the test specimen, and
  (b) measuring the slope of each curve generated in (a) above at time $t^*$ to provide polymerase reaction rates $C_1^i$ for each known polymerase activity $A_i$ and a polymerase reaction rate $C_1^x$ for the test specimen polymerase activity $A_x$, where $t^*$ is any given time, step B2) is carried out by plotting the rates $C_1^i$ determined in B1) as a function of the known polymerase activities $A_i$ to generate a calibration curve, and step B3) is carried out by projecting the test specimen rate $C_1^x$ generated in step B1) off the calibration curve generated in step B2) to determine $A_x$.

Thus, in this embodiment, one uses the detectable signals generated from the formation of a double-stranded DNA molecule to provide graphical plots of activity versus time for the known samples as well as the test specimen. The slopes of these curves at a given time are determined and plotted to provide a calibration curve from which $A_x$ is determined at the rate of reaction of the test specimen.

EMBODIMENT B

This embodiment is like Embodiment A in step B1), but steps B2) and B3) involve mathematical manipulations using standard calculus and algebraic operations. Thus, the slopes of the curves generated in B1) are manipulated mathematically, rather than graphically, to obtain $A_x$.

More specifically, step B1) is carried out by
- (a) generating curves from the colorimetric or fluorometric signals with time for each of the known polymerase activities, and generating a similar curve for the polymerase activity of the test specimen, and
- (b) measuring the slope of each curve generated in (a) above at time $t^*$ to provide polymerase reaction rates $C_1^i$ for each known polymerase activity $A_i$ and a polymerase reaction rate $C_1^x$ for the test specimen polymerase activity $A_x$, where $t^*$ is any given time, step B2 is carried out by regressing each polymerase rate $C_1^i$ generated in B1) versus the respective known polymerase activity $A_i$ using equation (I)

$$C_1 = \gamma_0 + \gamma_1 A + \gamma_2 A^2 + \gamma_3 A^3 \tag{I}$$

to obtain the coefficients $\gamma_0$, $\gamma_1$, $\gamma_2$, and $\gamma_3$, and step B3) is carried out by using the rate of test specimen polymerase activity $C_1^x$ and equation (II)

$$C_1^x = \gamma_0 + \gamma_1 A_x + \gamma_2 A_x^2 + \gamma_3 A_x^3 \tag{II}$$

to solve for $A_x$.

EMBODIMENT C

A further embodiment of this invention can be practiced by a method comprising the following sequence of steps. Obtaining the rates of reaction is accomplished mathematically rather than graphically as in Embodiments A and B. More specifically:

step B1) is carried out by
- (a) regressing the signal vs. time data for each known polymerase activity $A_i$ and for the unknown polymerase activity $A_x$ to obtain the regression coefficients of equation (III)

$$S^i = C_0^i + C_1^i t^* + C_2^i (t^*)^2 \tag{III}$$

wherein $S^i$ represents the colorimetric or fluorometric signal for a given time $t^*$ and known polymerase activity $A^i$, or unknown polymerase activity $A_x$, and $C_0^i$, $C_1^i$ and $C_2^i$ represent the regression coefficients,

- (b) taking the time derivative of equation (III) to obtain the rate according to equation (IV)

$$\left(\frac{dS}{dt}\right)_{t^*} = C_1^i + 2C_2^i t^* \tag{IV}$$

thereby providing the coefficient $C_1^i$ for each known polymerase activity $A_i$, the coefficient $C_1^i$ being the rate of polymerase activity $A_i$, step B2) is carried out by plotting the rates $C_1^i$ for the known polymerase activities determined in B1) as a function of the known polymerase activities $A_i$ to generate a calibration curve, and step B3) is carried out by projecting the test specimen rate $C_1^x$ generated in step B1) off the calibration curve generated in step B2) to determine $A_x$.

EMBODIMENT D

Still another way to practice the present invention includes the following mathematical manipulations:

step B1) is carried out by
- (a) regressing the signal vs. time data for each known polymerase activity $A_i$ and for the unknown polymerase activity $A_x$ to obtain the regression coefficients of equation (III)

$$S^i = C_0^i + C_1^i t^* + C_2^i (t^*)^2 \tag{III}$$

wherein $S^i$ represents the colorimetric or fluorometric signal for a given time $t^*$ and known polymerase activity $A_i$, or unknown polymerase activity $A_x$, and $C_0^i$, $C_1^i$ and $C_2^i$ represent the regression coefficients,

- (b) taking the time derivative of equation (III) to obtain the rate according to equation (IV)

$$\left(\frac{dS}{dt}\right)_{t^*} = C_1^i + 2C_2^i t^* \tag{IV}$$

thereby providing the coefficient $C_1^i$ for each known polymerase activity $A_i$, the coefficient $C_1^i$ being the rate of polymerase activity $A_i$, step B2 is carried out by regressing each polymerase rate $C_1^i$ generated in B1) versus the respective known polymerase activity $A_i$ using equation (I)

$$C_1 = \gamma_0 + \gamma_1 A + \gamma_2 A^2 + \gamma_3 A^3 \tag{I}$$

to obtain the coefficients $\gamma_0$, $\gamma_1$, $\gamma_2$, and $\gamma_3$, and step B3) is carried out by using the rate of test specimen polymerase activity $C_1^x$ and equation (II)

$$C_1^x = \gamma_0 + \gamma_1 A_x + \gamma_2 A_x^2 + \gamma_3 A_x^3 \tag{II}$$

to solve for $A_x$.

The mathematical calculations used in the various embodiments described above are standard and can be found in modern algebra and calculus textbooks. Their application to the present invention would be readily apparent to one skilled in the art in view of the teaching herein, such person having modest computational skills, or having readily available any of a number of commercial computer programs which would perform the needed computations.

The following examples illustrate the practice of the present invention, but are not meant to be limiting in any way. All percentages are by weight unless otherwise noted.

EXAMPLE 1

Assay for DNA Polymerase Using a Bibenzimidazole Fluorescent Dye and a Synthetic Oligonucleotide Template This example demonstrates the practice of this invention for the detection of a DNA polymerase isolated from Thermus aquaticus using a fluorescent dye.

Materials

The fluorometer used was a Perkin-Elmer LS-2 fluorometer with an autosampler. It was set for excitation of the dye at 366 nm and emission at 474 nm.

The fluorescent dye 2-[2-(4-hydroxyphenyl)-6-benzimidazole]-6-(1-methyl-4-piperazyl)benzimidazole trihydrochloride was obtained from CalBiochem. It has a molar extinction coefficient in water of $4.2 \times 10^4$ molar$^{-1}$cm$^{-1}$.

A primary dye stock solution was prepared in deionized water (1 mg/ml) and stored in the dark at 4° C. It is believed to be stable for up to 6 months in this environment. A secondary dye stock solution was prepared using a 1:50 dilution of the primary stock solution. This second solution was calibrated using an absorbance reading at 338 nm and the known molar extinction coefficient. It was then adjusted to $3.5 \times 10^{-5}$ molar (O.D.=1.45 at 338 nm) with either deionized water or the primary stock solution. The resulting solution was kept in the dark at 4° C. On the day of use, the stored solution was diluted 1:10 and kept in a 50 ml tube wrapped in aluminum foil to protect it from light. This working solution is stable at room temperature for at least a day.

The synthetic single-stranded oligonucleotide template was 125 nucleotides in length and was prepared and purified on an automated synthesizer using standard procedures. The template sequence was as follows (using standard abbreviations for the nucleotides, spacing used for convenience in reading the sequence):
5'-AAC CTC TGG GTC CAA GCC GTG GCC AGC GGC AGA CAT GGT TGA TAC CAA CCT GCA CAT TCT TAC TAT TTT ATT TAA TCC CAG GAT TGG GAT AGG TGG ATT ATT TGT GCA GAC TTC TCC TCA GGA GT-3'.

The template stock solution consisted of the template (2.5 μmolar) and dNTPs (3 mmolar, 0.75 mmolar of each) in assay buffer solution (described below).

The primer used had the following sequence (using standard nomenclature to identify the nucleotide bases):

5'-CTCCTGAGGAGAAGTCTGCACAA-3'

The primer stock solution consisted of primer (1.8 μmolar) and dNTPs (3 mmolar, 0.75 mmolar of each) in assay buffer solution.

The assay buffer solution consisted of potassium chloride (50 mmolar), tris(hydroxymethyl)aminomethane buffer (10 mmolar, pH 8.3), magnesium chloride (1.5 mmolar) and gelatin (0.01%).

A dilution buffer for the DNA polymerase isolated from *Thermus aquaticus* strain YT-1 (available as ATCC 25,104 from the American Type Culture Collection, Rockville, Maryland) consisted of tris(hydroxymethyl)aminomethane buffer (25 mmolar, pH 8), potassium chloride (50 mmolar), gelatin (500 μg/ml), β-mercaptoethanol (1 mmolar), Nonidet ™ NP-40 nonionic surfactant (0.5%) and Tween ™ 20 nonionic surfactant (0.5%).

Assay

The primer and template were hybridized by mixing the template stock solution (300 μl) and primer stock solution (700 μl) and incubating at 42° C. for 4 hours. The resulting mixture of hybridized product was then cooled in ice (0° C.), and mixed with the DNA polymerase (4 units/μl, diluted to 0.4 units/μl according to following procedure to form reactions mixtures:

| Tube | Hybridization Mixture Volume (μl) | DNA Polymerase Solution Volume (μl) | Final DNA Polymerase Concentration |
|---|---|---|---|
| 1 | 855 | 45 | 20 units/ml |
| 2 | 889 | 11 | 4.9 units/ml |
| 3 | 900 | 1 | 0.49 units/ml |

A unit of DNA polymerase corresponds to the amount of enzyme which can incorporate 10 mmoles of total nucleotides into an acid-precipitable product using activated DNA as a template in 30 seconds at 70° C., in a solution comprising potassium chloride (50 mmolar), tris(hydromethyl)aminomethane buffer (10 mmolar, pH 8.3) magnesium chloride (1.5 mmolar) and dNTPs (0.75 mmolar total).

Each reaction mixture (100 μl) was put into separate tubes and stored at 0° C. The extension reactions were then initiated by removing the reaction mixture samples from ice and placing them in a water bath heated to 60° C. At selected time intervals (0, 3, 6, 9 and 12 minutes), duplicate tubes containing reaction mixture (100 μl) having different DNA polymerase concentrations were taken from the water bath and placed in ice (0° C.). From each tube, three separate aliquots (25 μl) were mixed with the dye solution (1 ml) and the relative fluorescence was measured.

The results of these tests are shown in FIG. 1A as a graphical plot of the change in relative fluorescence versus the time for duplicate tests at the three different DNA polymerase concentrations.

The data depicted in FIG. 1A was regressed in time according to the following equation:

$$S^i = C_0^i + C_1^i t + C_2^i t^2$$

with the results provided in the following Table:

TABLE I

| i | $A_i$ (Units/ml) | $C_1^i$ (f/min.)* |
|---|---|---|
| 1 | 0.5 | 1.48 |
| 2 | 5 | 9.45 |
| 3 | 20 | 24.5 |

*f = relative fluorescence

The initial rates ($C^i$) were then plotted versus polymerase activities, as shown in FIG. 1B. These data (that is, the $C^i$) were in turn regressed versus polymerase activities ($A_i$) according to the following equation (which represents the solid line in FIG. 1B):

$$C_1^i = \gamma_0 + \gamma_1 A + \gamma_2 A^2$$

yielding the following regression coefficients:
$\gamma_0 = 0.50$
$\gamma_1 = 1.99$ and
$\gamma_2 = -0.0394$.

As an example as to how the immediately preceeding equation could be used to determine the amount of polymerase in a test sample in view of a known enzymatic rate, one could consider a rate of 15 (f/min). Using FIG. 1B, this rate corresponds to a polymerase concentration of about 8.7 units/ml.

Alternatively, this same result can be obtained using standard mathematical calculations and solving the following equation for $A_x$ (activity):

$$A_x = \frac{-\gamma_1 - \sqrt{\gamma_1^2 - 4(\gamma_2)(\gamma_0 - C_1)}}{2\gamma_2}$$

wherein for a $C_1$ of 15 f/min (initial rate), A is determined to be about 8.8 units/ml.

This example shows that DNA polymerase concentrations can be effectively determined using the method of the present invention and the bibenzimidazole fluorescent dye described herein. This determination can be carried out using either a plotted calibration curve, or standard mathematical calculations.

EXAMPLE 2

Assay for DNA Polymerase Using a M13 Template and Fluorescent Dye

This example is similar to Example 1 except a naturally occuring phage DNA was used as a template. A number of other minor changes were also made.

Materials

The fluorometer used was a Perkin Elmer LS-2 fluorometer which was modified to handle sample that were loaded automatically using a Perkin Elmer Multi-Sampler. The flow cell and the tubing in the equipment held about 1 ml of solution. Triplicate readings were taken at each point in time.

The dye solution was prepared as described in Example 1.

The template used was single-strand M13 mpO/T-SYC 657-8 obtained from Cetus Corp.

The primer had the following nucleotide sequence (using standard base identification):

5'-CCCGGGCGGCGCCGCAGCGGCGGG-3'

The primer extension reaction mixture comprised the following:

primer (0.26 μmolar), template (13 nmolar), DNA polymerase isolated from *Thermus aquaticus* (20 units/ml, with 1 unit defined above), dNTPs (1.5 mmolar of each) which are added last to begin extension (see below), gelatin (1 mg/ml), potassium chloride (50 mmolar), ethylenediaminetetraacetic acid (1 mmolar), tris(-hydroxymethyl)aminomethane buffer (10 mmolar, pH 8) and magnesium chloride (8, 10 and 13 mmolar).

Assay

The primer and template were hybridized, after which the dNTP's (60 μl, 100 mmolar total triphosphates) were added to the reaction mixture (1 ml, yielding a final dNTP concentration of 6 mmolar) at 75° C. As noted above, this addition of the dNTP's initiated the reaction. The temperature was maintained at 75° C. for 12 minutes. At selected times (1, 2, 3, 10, 11 and 12 minutes), aliquots (150 μl) were removed and added to vials which had been precooled in a brine mixture (0° C.) to quench the reaction. The dye solution (1 ml of solution containing 0.1 μg/ml) was placed in glass tubes, the cold reaction solution (10 μl) was added and the tubes were vortexed thoroughly to mix the solutions. Triplicate solutions (about 1 ml) were placed in the fluorometer. This procedure was carried out at three different magnesium ion concentrations in the reaction mixture (8, 10 and 13 mmolar).

Figure 2:
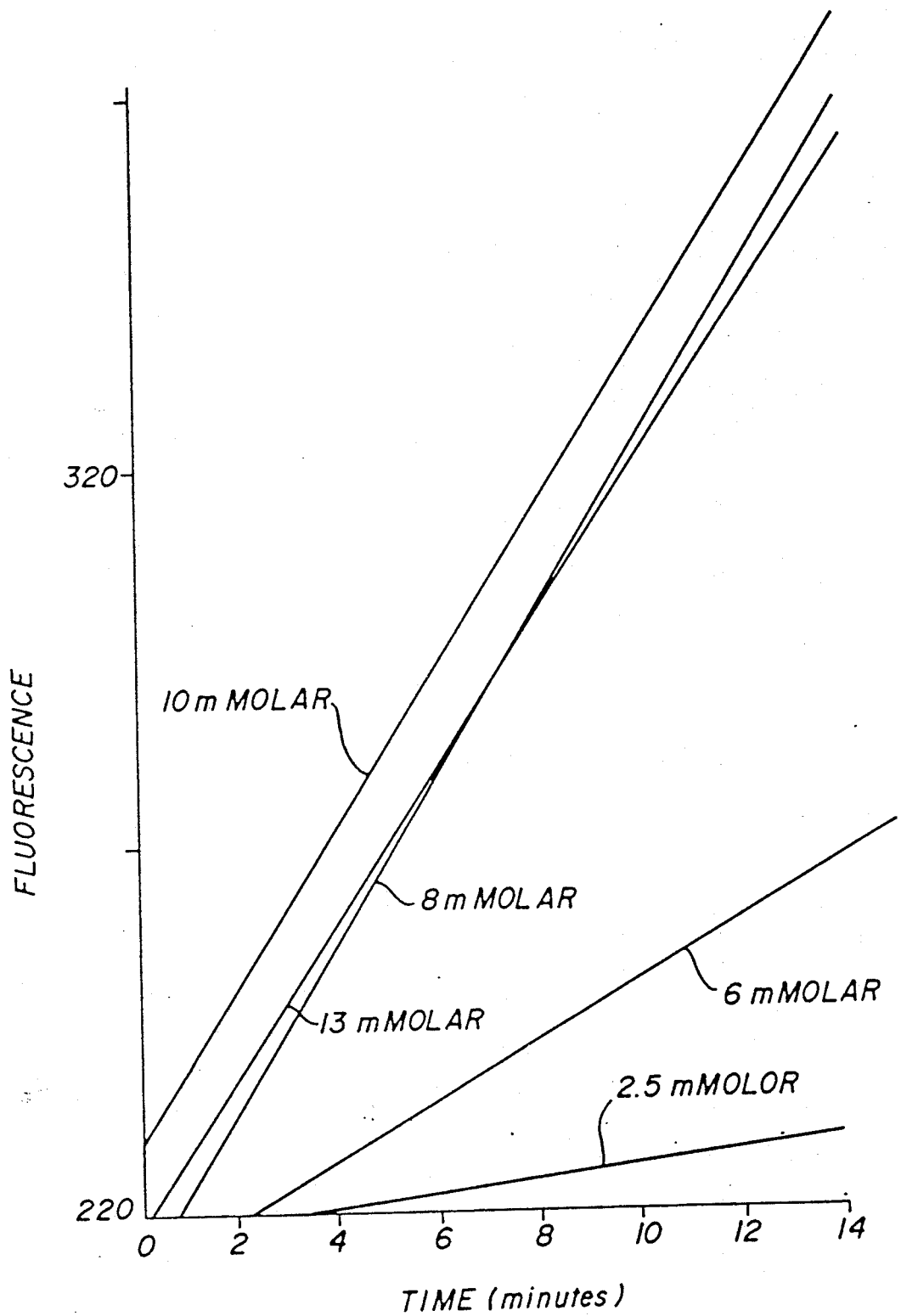
FIG. 2 is a graphical plot of fluorescence versus time at three different magnesium ion concentrations. These data are described in more detail in Example 2 below.
Figure 3:
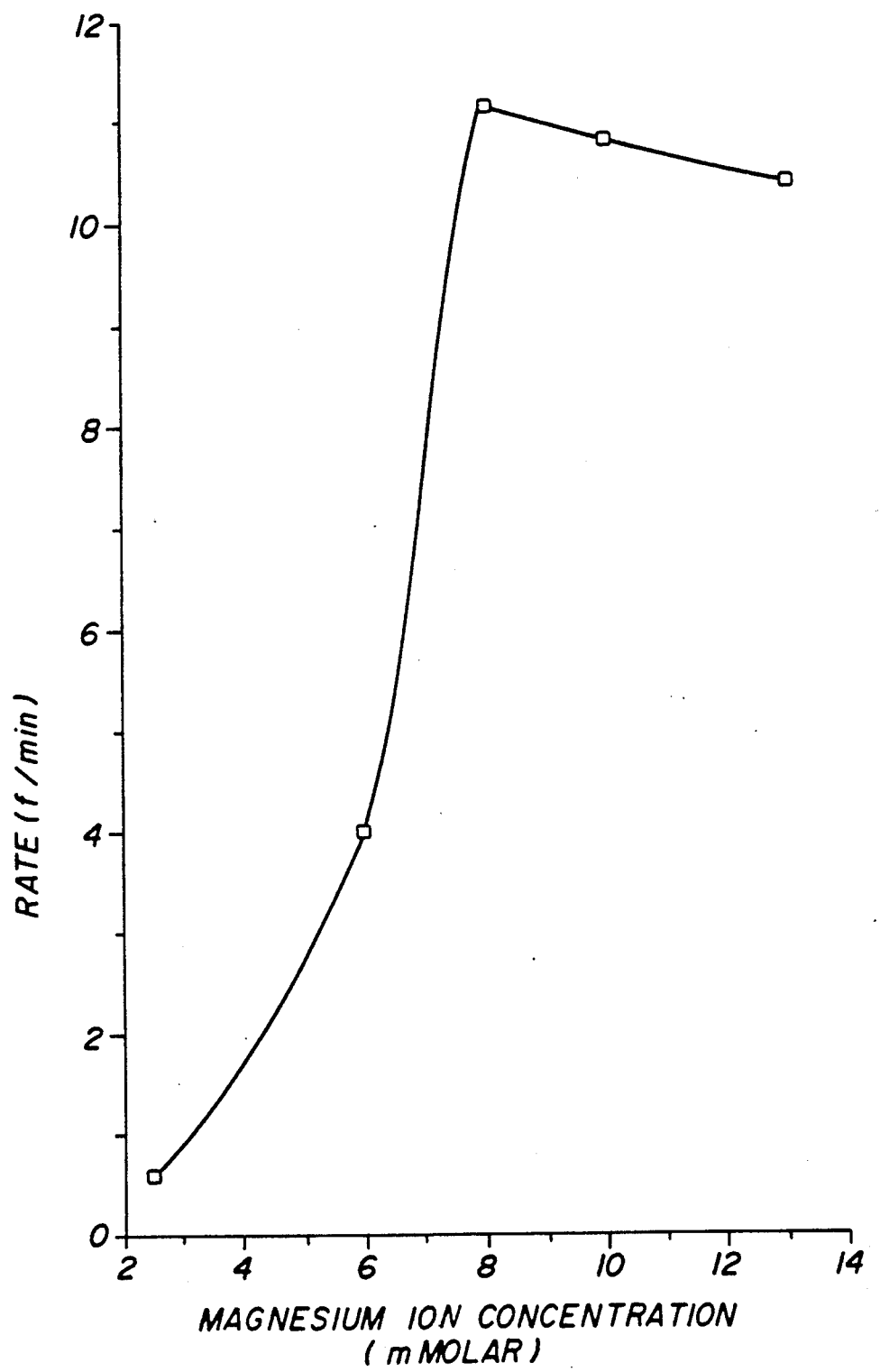
FIG. 3 is a graphical plot of the rate of change in fluorescent versus magnesium ion concentrations for the data presented in FIG. 2.

The results are shown in the graphical plots of FIG. 2 as plots of fluorescence versus time. The slopes (reaction rates) of these curves were then plotted versus magnesium ion concentration in FIG. 3. These data indicate that a 8 mmolar concentration of magnesium ion gives the fastest rate of reaction.

EXAMPLE 3

Assay for DNA Polymerase Using Bibenzimidazole and Ethidium Bromide Fluorescent Dyes and M13 Phage DNA Template This example illustrates the use of two different dyes in the method of this invention.

Materials

The fluorometer used was a Perkin Elmer LS-5B, equipped with a Perkin Elmer Multi-Sampler. The fluorometer was set at an excitation of 342 nm and emission of 474 nm for the bibenzimidazole, and at an excitation of 312 nm and emission of 580 nm for ethidium bromide.

Assay reagents were prepared or obtained as described in Example 1, except that the DNA polymerase concentration was 25 units/ml.

The primer had the following sequence:

5'-GAGCCACCACCGGAACCGCCTCCCT-CAGAGCCGCCACCCT-3'.

Assay

Each dye solution was put into separate sets of test tubes and evaluated separately.

The primer and template were hybridized as described in Example 1. The tubes containing 100 μl of reaction mixture were stored at 0° C. Primer extension reactions were then initiated by removing the reaction mixtures from the low temperature environment and placing them into water maintained at 60° C. At selected times (4, 4.5, 5, 13, 13.5 and 14 minutes), tubes were taken from the water bath and placed in ice (0° C.). From each tube, three separate aliquots (25 μl) were mixed with each dye solution (1 ml) separately and the relative fluorescence measured.

The results of these tests are shown in the Table below. They indicate that, while the bibenzimidazole is more sensitive, ethidium bromide is also useful in the practice of this invention.

| Time (minutes) | Relative Fluorescence | |
| --- | --- | --- |
| | Bibenzimidazole | Ethidium Bromide |
| 4 | 599 | 172 |
| 4.5 | 632 | 182 |
| 5 | 663 | 183 |
| 13 | 913 | 227 |
| 13.5 | 912 | 230 |
| 14 | 930 | 228 |

EXAMPLES 4 and 5

Determination of Polymerase Activity in Two Samples

These examples are similar to Example 1 except M13 phage DNA was used as a template and a number of other changes were made.

Materials

The fluorometer used was a Perkin Elmer LS-5B fluorometer which was modified to handle samples that were loaded automatically using a Perkin Elmer Multi- Sampler. The flow cell and the tubing in the equipment held about 1 ml of solution. Triplicate readings were taken at each point in time.

The dye solution was prepared as described in Example 1.

The template used was single-strand M13mp18 available from International Biotechnologies, Inc. (New Haven, Conn., catalog #77242).

The primer had the following nucleotide sequence (using standard base identification):

5'-GAGCCACCACCGGAACCGCCTCCCT-CAGAGCCGCCACCCT-3'

The primer extension reaction mixture comprised the following:

primer (0.07 μmolar), template (16 nmolar), DNA polymerase isolated from *Thermus aquaticus* (having activities stated below), dNTPs (0.5 mmolar of each), gelatin (1 mg/ml), ethylenediaminetetraacetic acid (1 mmolar), tris(hydroxymethyl)aminomethane buffer (10 mmolar, pH 8) and magnesium chloride (6 mmolar).

Assay

The primer and template were hybridized, after which the dNTP's and DNA polymerase were added to the reaction mixture. An sharp increase in temperature (from 0° C. to 75° C.) was used to initiate the reaction. The temperature was maintained at 75° C. for 14 minutes. At selected times (3, 3.5, 4, 13.5 and 14 minutes), aliquots (150 μl) were removed and added to vials which had been precooled in a brine mixture (0° C.) to quench the reaction. The dye solution (1 ml of solution containing 0.1 μg/ml) was placed in glass tubes, the cold reaction solution (10 μl) was added and the tubes were vortexed thoroughly to mix the solutions. Triplicate solutions (about 1 ml) were placed in the fluorometer. This procedure was carried out at five different DNA polymerase concentrations (0, 5, 7.5, 15 and 25 units/ml) in the reaction mixture.

Figure 4:
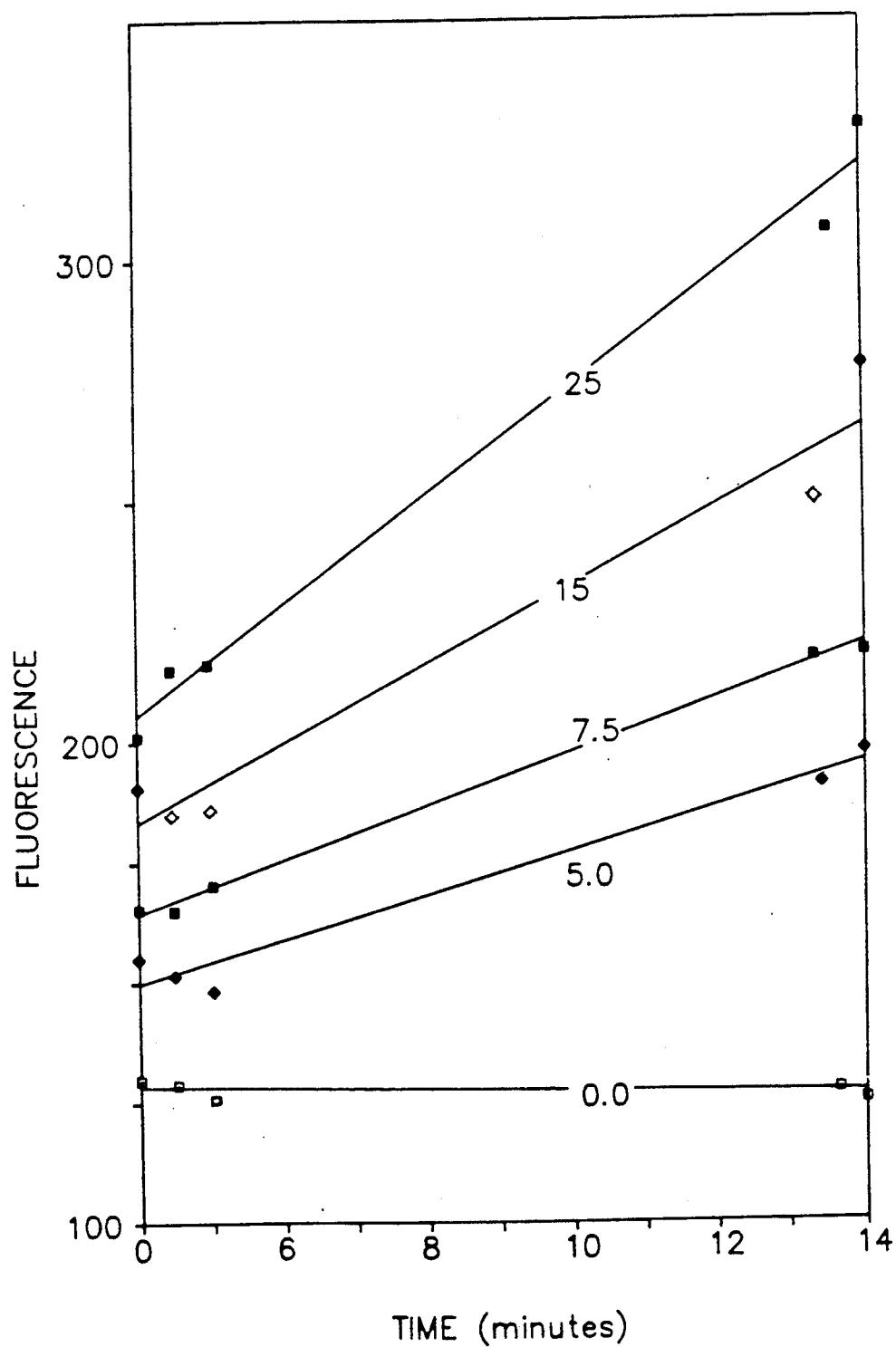
FIG. 4 is a graphical plot of fluorescence generated over time for several known concentrations of DNA polymerase. It is discussed in more detail in Examples 4 and 5 below.

The results are shown in the graphical plots of FIG. 4 as plots of fluorescence versus time at various polymerase concentrations. The slopes of these curves were then plotted versus DNA polymerase concentration as a calibration curve in FIG. 5. The slopes of the plots were calculated by linear regression according to Equation (I). The regression coefficients ($C^i$) are listed in the following Table II:

TABLE II

| i | $A_i$ (Units/ml) | $C^i$ (f/min.)* |
|---|---|---|
| 1 | 0 | −0.21 |
| 2 | 5 | 4.62 |
| 3 | 7.5 | 5.60 |
| 4 | 15 | 8.32 |
| 5 | 25 | 11.55 |

*f = relative fluorescence

When these initial rates were regressed against the known activities ($A_i$) according to Equation (III), the following regression coefficients were obtained:
$\gamma_0 = 0.261$
$\gamma_1 = 0.790$
$\gamma_2 = -0.0138$ and
$\gamma_3 = 0$,
that is, $$C_1 = 0.261 + 0.790\,A - 0.0138\,A^2$$

The foregoing equation can be inverted to permit determination of unknown activities $A_x$ from known rates ($C_i$) as follows:

$$A_x = \frac{0.790 - \sqrt{(0.790)^2 - 4(0.0138)(C_1 - 0.261)}}{2(0.0138)}$$

Figure 6:
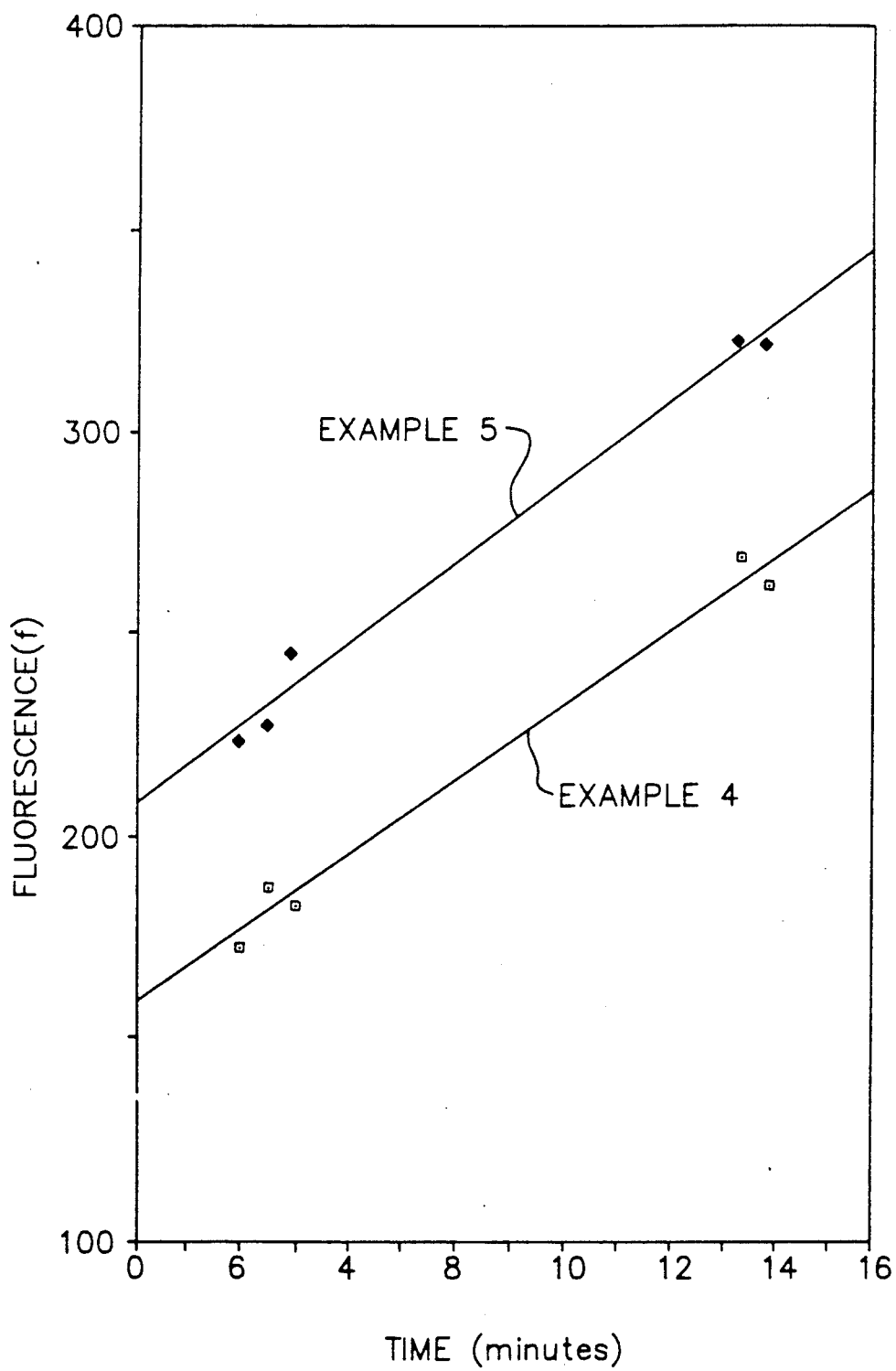
FIG. 6 is a graphical plot of the fluorescence observed over time for time samples of unknown DNA polymerase concentration as described in Examples 4 and 5 below.

Two different samples containing unknown amounts of DNA polymerase were also tested according to the same procedure described above. One sample was purchased from International Biotechnologies, Inc. (Example 4, identified commercially by catalog #19010). A second sample (Example 5) was a recombinant form of the enzyme commercially available from Cetus Corp. Graphical plots of the resulting fluorescence versus time are shown in FIG. 6.

Relative fluorescence readings for Examples 4 and 5 were regressed versus time, leading to the following two equations:

Example 4: $f = 140 + 9.11t$ (t=time)

Example 5: $f = 187 + 9.86t$ (t=time)

The initial rates were computed using Equation (III), as follows:

Example 4: $\left(\frac{df}{dt}\right)_{t=0} = C_1 = 9.11$ (f/min.)

Example 5: $\left(\frac{df}{dt}\right)_{t=0} = C_1 = 9.86$ (f/min.)

Figure 7:
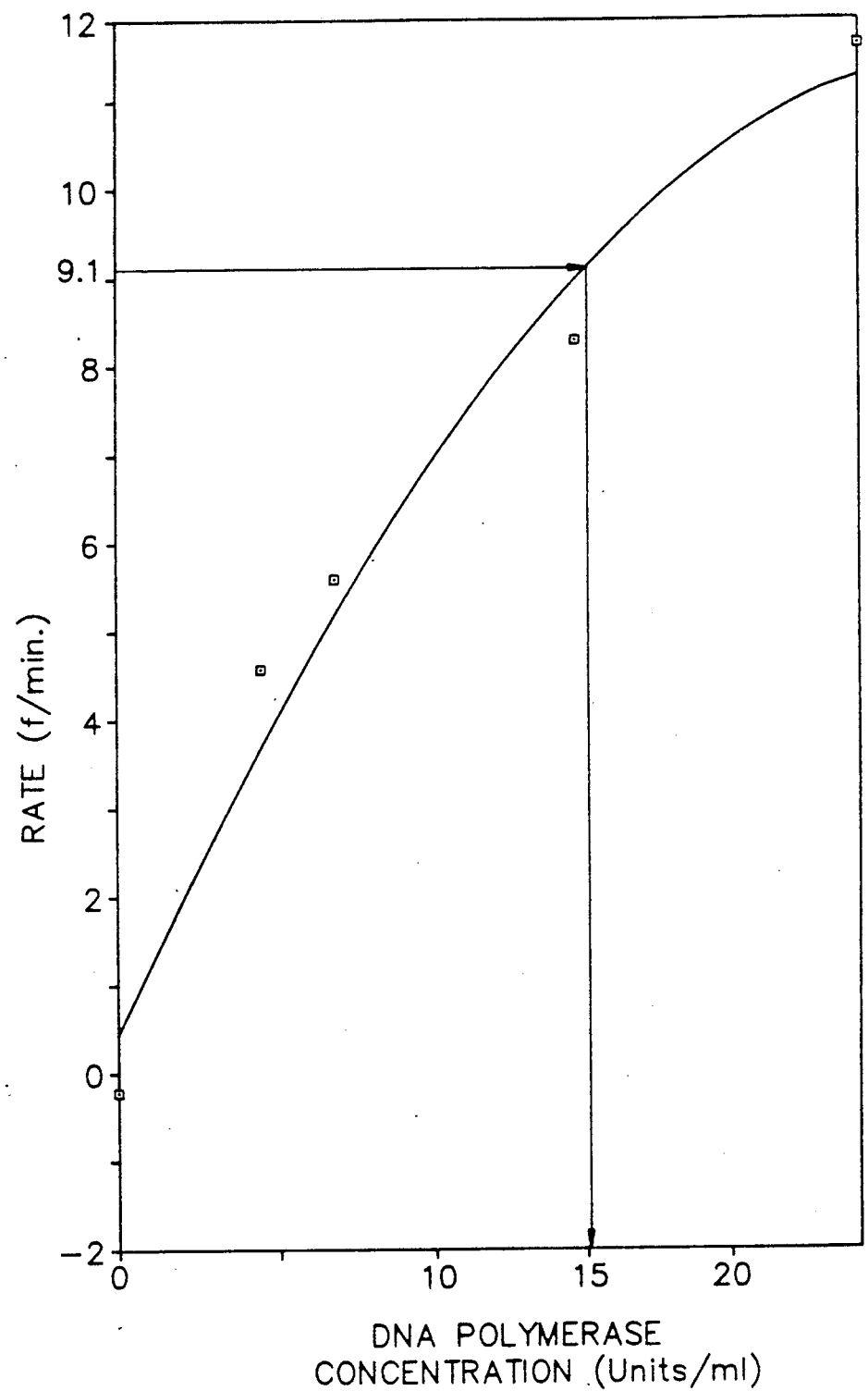
FIGS. 7 and 8 are graphical plots of rate of fluorescence change versus DNA polymerase concentration for unknown DNA polymerase samples of Examples 4 and 5, respectively.
Figure 8:
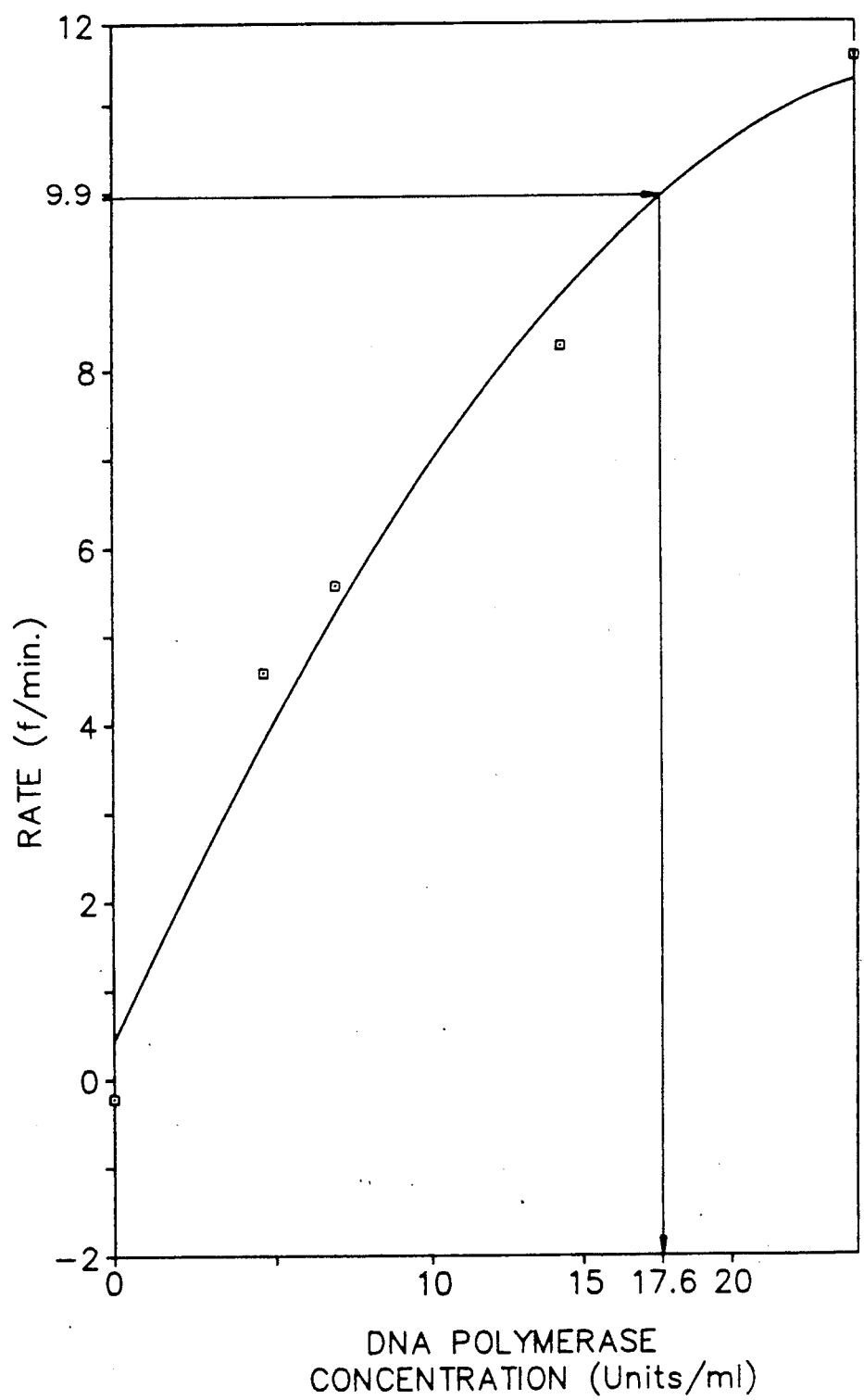

These two rates were then projected graphically off the calibration curve (FIG. 5), as shown on FIGS. 7 and 8, respectively for Examples 4 and 5. The estimated DNA polymerase concentrations for each sample were: 15 units/ml for Example 4 and 17.6 units/ml for Example 5.

When the rates (9.11 and 9.86 f/min. for Examples 4 and 5, respectively) were inserted into the terms of Equation (IV), the following results were obtained:
Example 4: about 15.3 units/ml, and
Example 5: about 17.5 units/ml.

Figure 5:
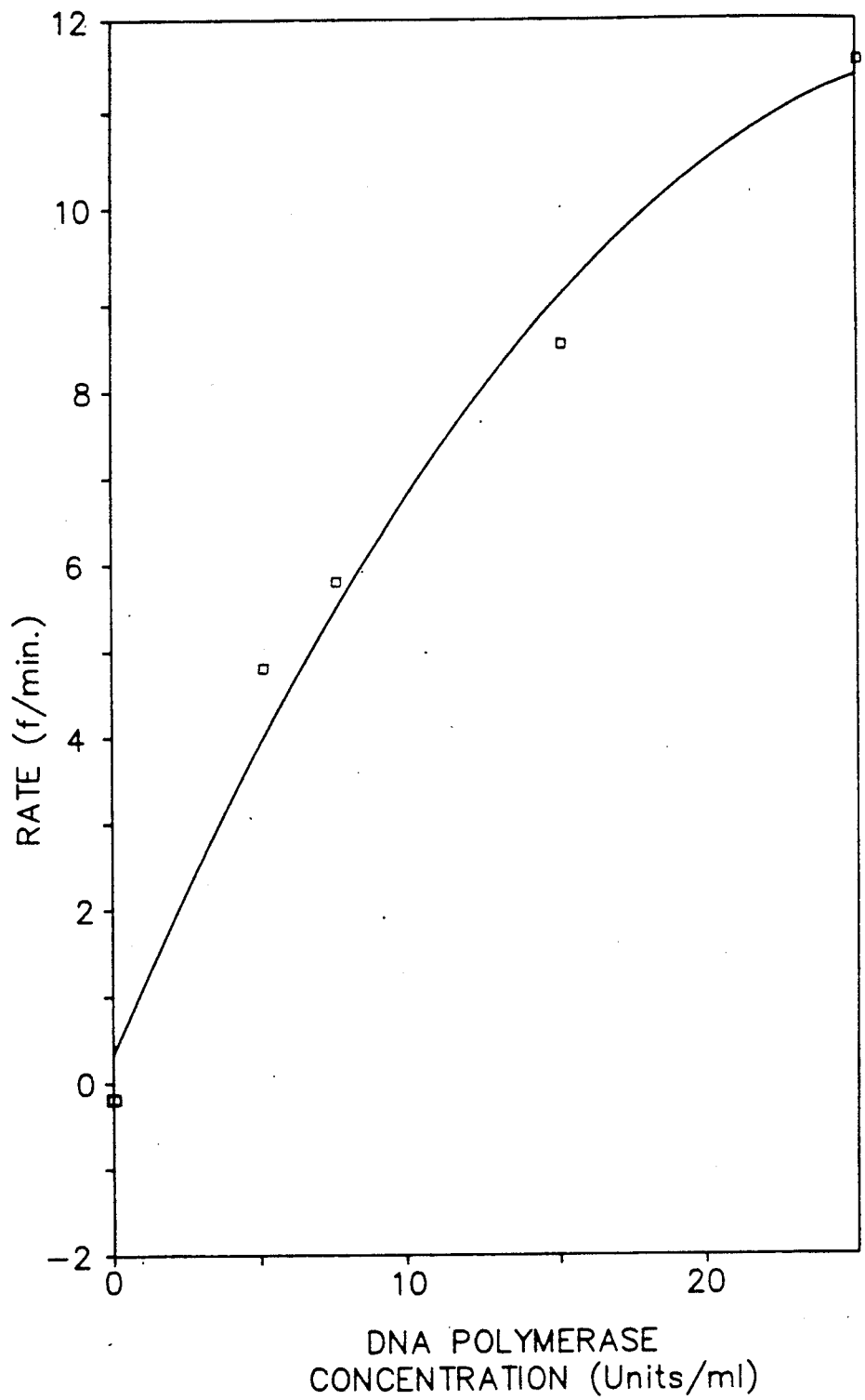
FIG. 5 is a calibration curve generated in Examples 4 and 5 below of rate of fluorescence change versus DNA polymerase concentration.

The results correspond well to those obtained from the calibration curve (FIG. 5). These examples demonstrate that unknown concentrations of DNA polymerase can be determined using the method of this invention, either by using a calibration curve, or by strict mathematical treatment of experimental data.

EXAMPLE 6

Assay Carried Out with Premixed Flourescent Dye

This example illustrates the practice of the present invention wherein the fluorescent dye was mixed with the template and other polymerization reagents prior to contact with the DNA polymerase to be detected. The polymerase chain reaction was then initiated by the addition of aliquots of DNA polymerase, and fluorescent signals were measured continuously over time. This procedure has some advantages in that it allows more samples to be tested in a given time, and more dye signal measurements can be made. Thus there is more potential for higher precision as sampling and handling errors are minimized.

Materials

The template was a single-stranded M13 DNA phage obtained from IBI (New Haven, Conn.).

The fluorescent dye solution used was that shown in Example 1.

The polymerase chain reaction reagent solution contained: bovine serum albumin (30 μl, 2%), buffer solution (30 μl of 100 mmolar, pH 8.5), magnesium chloride (36 μl, 100 μmolar), template (37.9 μl, 0.25 μmolar), primer (1.9 μl), dNTPs (100 μmolar each, 12 μl) and water (149 μl). The primer had the sequence:

5'-GAGCCACCACCGGAACCGCCTCCCT-CAGAGCCGCCACCCT-3'

The buffer solution noted above contained tris(hydroxymethyl)aminomethane buffer (10 mmolar, pH 8.3), magnesium chloride (1.5 mmolar) and gelatin (0.01%).

Assay

The fluorescent dye solution (300 μl) was mixed with the polymerase chain reaction reagent solution (297 μl). The resulting mixture was placed in a LS-5B fluorometer after the mixture was equilibrated at 62° C.

Figure 9:
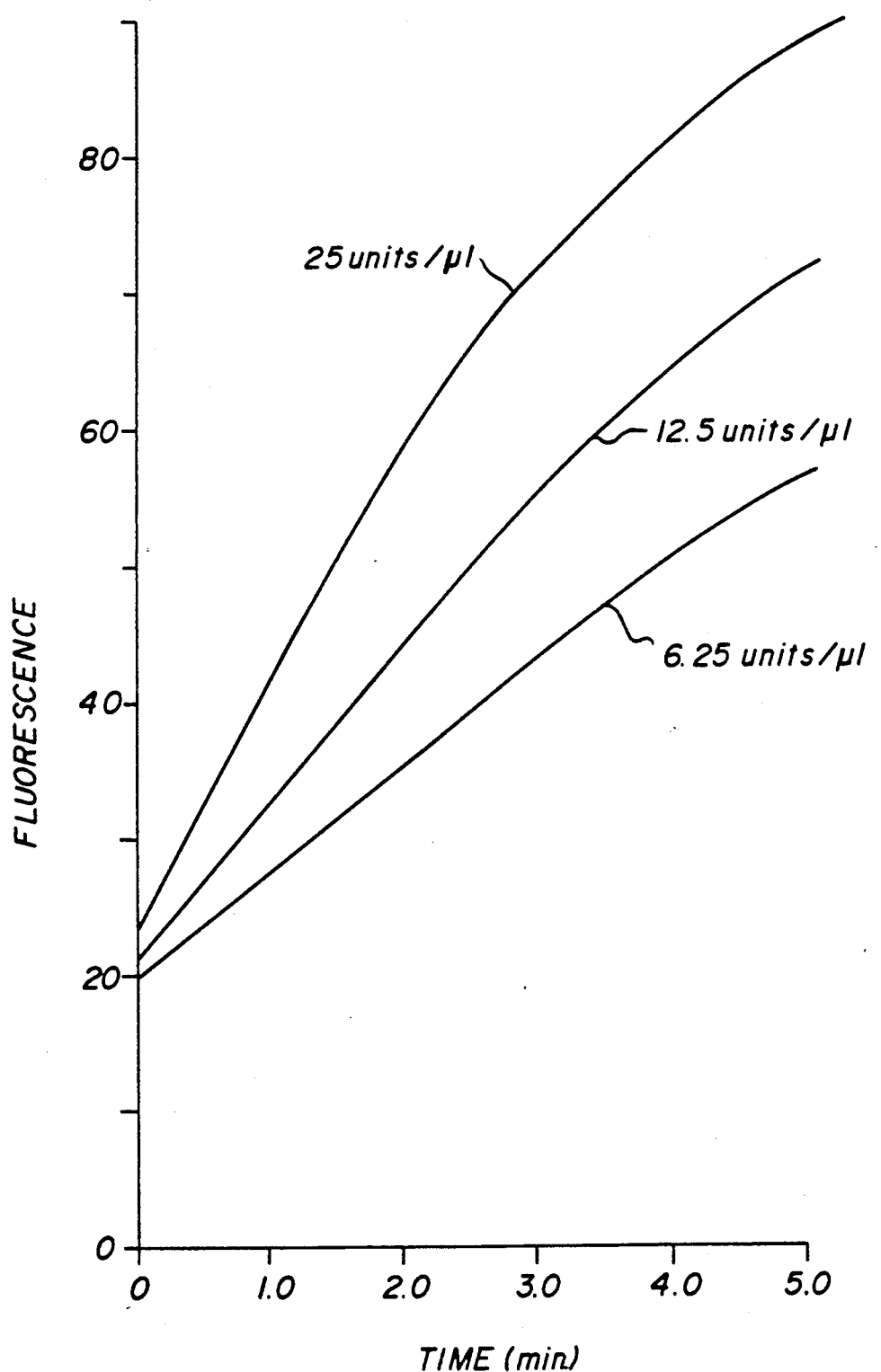
Figure 10:
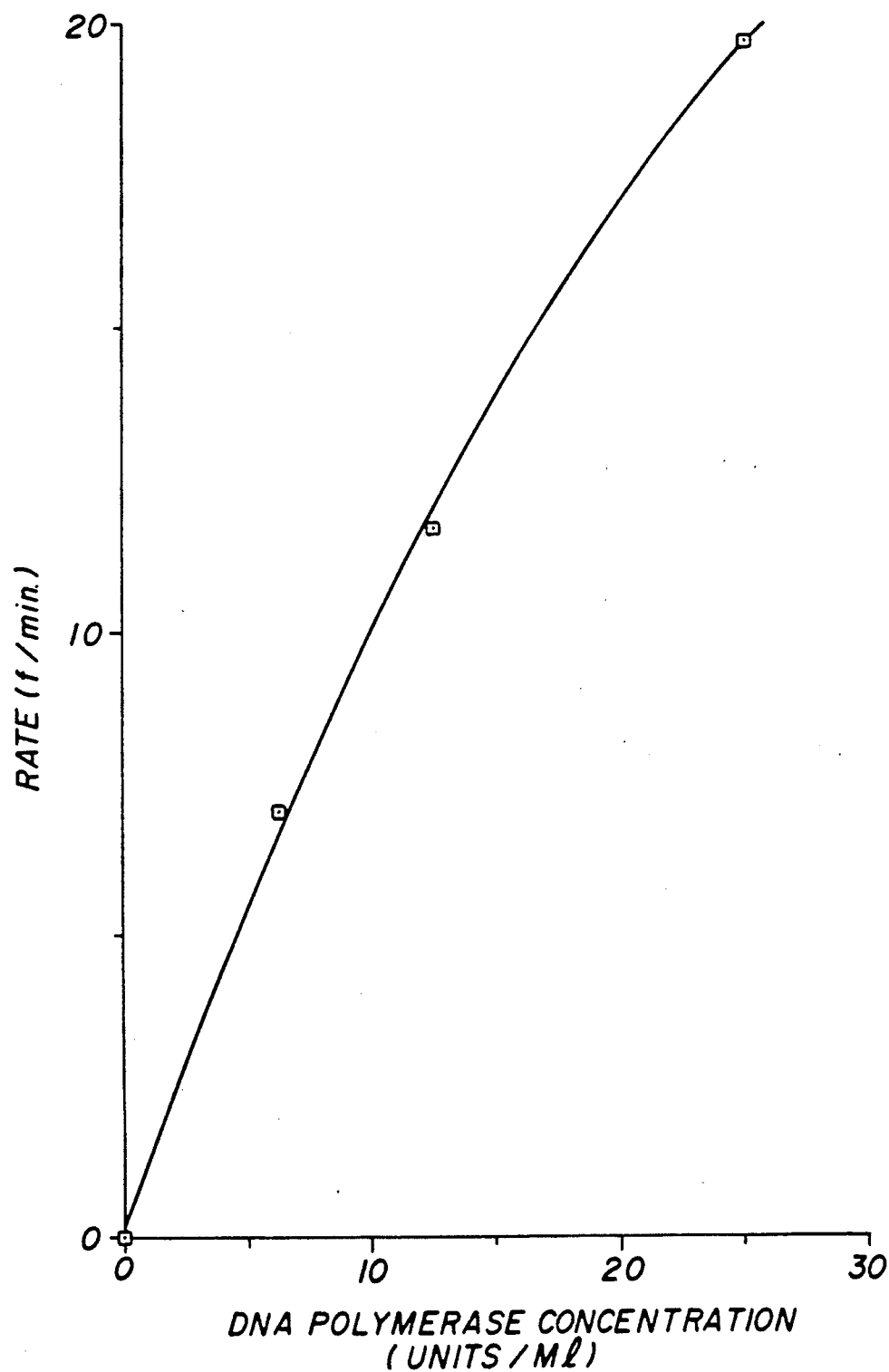

Reaction was initiated by adding a solution of DNA polymerase (isolated from *Thermus aquaticus* as identified above in Example 1) at various concentrations (3.75 μl having 25 units/μl, 1.88 μl having 12.5 units/μl and 0.94 μl having 6.25 units/μl). Fluorescence was measured for each polymerase concentration at various times. No fluorescence change was observed with a Control solution (buffer only, no DNA polymerase). The resulting data was plotted as shown in FIG. 9. The initial rates were obtained from the graphical curves of FIG. 9 by graphical measurement, and plotted as shown in FIG. 10. Good correlation of the initial rates and DNA polymerase activity can be seen from these data.

The invention has been described in detail with particular reference to preferred embodiments thereof, but it will be understood that variations and modifications can be effected within the spirit and scope of the invention.

We claim:

1. A method for the quantitative determination of a DNA polymerase, comprising:
   A. bringing into contact:
      an aqueous test specimen believed to contain a DNA polymerase having activity $A_x$,
      a single-stranded DNA template which is present in a concentration of at least about $10^{-8}$ molar nucleotides,
      a DNA primer complementary to said template,
      a polymerase metal ion cofactor,
      sufficient deoxyribonucleoside triphosphates to generate a double-stranded DNA molecule from said template in the presence of said polymerase, and
      a colorimetric or fluorescent dye which, when bound to said double-stranded DNA formed from said template, exhibits a detectable signal as opposed to when said dye is bound to said template, and
   B. determining, with a precision having a covariance of less than about 10%, the activity $A_x$ of said polymerase in said test specimen corresponding to the rate of colorimetric or fluorometric signal generated by the binding of said dye to the double-stranded DNA formed by the action of said test specimen polymerase,
   said polymerase activity $A_x$ being determined as follows:
   1) generating polymerase rates of reaction from the colorimetric or fluorometric signals generated over time by each of a series of samples containing DNA polymerase having known polymerase activities, $A_1, A_2, \ldots A_i \ldots A_n$ wherein n is the number of samples evaluated and is at least two, and generating the polymerase rate of reaction from the colorimetric or fluorometric signal generated over time from said test specimen,
   2) determining a calibration using said rates of step 1) and said known polymerase activities $A_i$, and
   3) predicting $A_x$ using the calibration of step 2) and said polymerase reaction rate of said test specimen.

2. The method of claim 1 wherein:
   step B1) is carried out by
      (a) generating curves from said colorimetric or fluorometric signals with time for each of said known polymerase activities, and generating a similar curve for the polymerase activity of said test specimen, and
      (b) measuring the slope of each curve generated in (a) above at time t* to provide polymerase reaction rates $C_1^i$ for each known polymerase activity $A_i$ and a polymerase reaction rate $C_1^x$ for said test specimen polymerase activity $A_x$, where t* is any given time,
   step B2) is carried out by plotting the rates $C_1^i$ determined in B1) as a function of the known polymerase activities $A_i$ to generate a calibration curve, and
   step B3) is carried out by projecting said test specimen rate $C_1^x$ generated in step B1) off the calibration curve generated in step B2) to determine $A_x$.

3. The method of claim 1 wherein:
   step B1) is carried out by
      (a) generating curves from said colorimetric or fluorometric signals with time for each of said known polymerase activities, and generating a similar curve for the polymerase activity of said test specimen, and
      (b) measuring the slope of each curve generated in (a) above at time t* to provide polymerase reaction rates $C_1^i$ for each known polymerase activity $A_i$ and a polymerase reaction rate $C_1^x$ for said test specimen polymerase activity $A_x$, where t* is any given time,
   step B2 is carried out by regressing each polymerase rate $C_1^i$ generated in B1) versus the respective known polymerase activity $A_i$ using equation (I)

$$C_1 = \gamma_0 + \gamma_1 A + \gamma_2 A^2 + \gamma_3 A^3 \qquad (I)$$

to obtain the coefficients $\gamma_0, \gamma_1, \gamma_2,$ and $\gamma_3$, and
   step B3) is carried out by using the rate of test specimen polymerase activity $C_1^x$ and equation (II)

$$C_1^x = \gamma_0 + \gamma_1 A_x + \gamma_2 A_x^2 + \gamma_3 A_x^3 \qquad (II)$$

to solve for $A_x$.

4. The method of claim 1 wherein:
   step B1) is carried out by (a) regressing the signal vs. time data for each known polymerase activity $A_i$ and for said unknown polymerase activity $A_x$ to obtain the regression coefficients of equation (III)

$$S^i = C_0^i + C_1^i t^* + C_2^i (t^*)^2 \qquad \text{(III)}$$

wherein $S^i$ represents the colorimetric or fluorometric signal for a given time $t^*$ and known polymerase activity $A_i$, or unknown polymerase activity $A_x$, and $C_0^i$, $C_1^i$ and $C_2^i$ represent the regression coefficients, (b) taking the time derivative of equation (III) to obtain the rate according to equation (IV)

$$\left(\frac{dS}{dt}\right)_{t^*} = C_1^i + 2C_2^i t^* \qquad \text{(IV)}$$

thereby providing the coefficient $C_1^i$ for each known polymerase activity $A_i$, said coefficient $C_1^i$ being the rate of polymerase activity $A_i$, step B2) is carried out by plotting the rates $C_1^i$ for the known polymerase activities determined in B1) as a function of the known polymerase activities $A_i$ to generate a calibration curve, and step B3) is carried out by projecting said test specimen rate $C_1^x$ generated in step B1) off the calibration curve generated in step B2) to determine $A_x$.

5. The method of claim 1 wherein:

step B1) is carried out by (a) regressing the signal vs. time data for each known polymerase activity $A_i$ and for said unknown polymerase activity $A_x$ to obtain the regression coefficients of equation (III)

$$S^i = C_0^i + C_1^i t^* + C_2^i (t^*)^2 \qquad \text{(III)}$$

wherein $S^i$ represents the colorimetric or fluorometric signal for a given time $t^*$ and known polymerase activity $A_i$, or unknown polymerase activity $A_x$, and $C_0^i$, $C_1^i$ and $C_2^i$ represent the regression coefficients, (b) taking the time derivative of equation (III) to obtain the rate according to equation (IV)

$$\left(\frac{dS}{dt}\right)_{t^*} = C_1^i + 2C_2^i t^* \qquad \text{(IV)}$$

thereby providing the coefficient $C_1^i$ for each known polymerase activity $A_i$, said coefficient $C_1^i$ being the rate of polymerase activity $A_i$, step B2 is carried out by regressing each polymerase rate $C_1^i$ generated in B1) versus the respective known polymerase activity $A_i$ using equation (I)

$$C_1 = \gamma_0 + \gamma_1 A + \gamma_2 A^2 + \gamma_3 A^3 \qquad \text{(I)}$$

to obtain the coefficients $\gamma_0$, $\gamma_1$, $\gamma_2$, and $\gamma_3$, and step B3) is carried out by using the rate of test specimen polymerase activity $C_1^x$ and equation (II)

$$C_1^x = \gamma_0 + \gamma_1 A_x + \gamma_2 A_x^2 + \gamma_3 A_x^3 \qquad \text{(II)}$$

to solve for $A_x$.

6. The method of claim 1 wherein n is from 2 to 5.

7. The method of claim 1 for the detection of a polymerase obtained from *Thermus aquaticus*.

8. The method of claim 1 wherein said test specimen is mixed with said template, DNA primer, cofactor and deoxyribonucleoside triphosphates prior to contact with said colorimetric or fluorometric dye.

9. The method of claim 1 wherein said dye is a fluorescent dye selected from the group consisting of bibenzimidazole, ethidium, methidium and acridine dyes.

10. The method of claim 9 wherein said fluorescent dye is a bibenzimidazole dye.

11. The method of claim 1 wherein said fluorescent dye is selected from the group consisting of 2-[2-(4-hydroxyphenyl)-6-benzimidazole]-6-(1-methyl-4-piperazyl)benzimidazole trihydrochloride, acridine orange, methidium bromide, propidium iodide, ethidium bromide and 4′,6′-diamidino-2-phenylindole.

12. The method of claim 1 wherein said detectable signal is an increase in fluorometric signal.

13. The method of claim 1 wherein said detectable signal is a change in $\lambda_{max}$ of said colorimetric dye.

14. The method of claim 1 wherein said DNA template is M 13 phage.

15. A method for the quantitative determination of a thermostable DNA polymerase isolated from *Thermus aquaticus*, comprising:

A. bringing into contact:

an aqueous test specimen believed to contain a thermostable DNA polymerase isolated from *Thermus aquaticus*, or a clone from a genome thereof, having activity $A_x$, single-stranded M 13 phage DNA as a template which is present in a concentration of at least about $10^{-8}$ molar nucleotides, a DNA primer complementary to said template, a source of magnesium ion, sufficient deoxyribonucleoside triphosphates to generate a double-stranded DNA molecule from said template in the presence of said polymerase, and a bibenzimidazole dye which exhibits a detectable fluorometric signal when bound to said double-stranded DNA formed from said template, as opposed to when said dye is bound to said template, and B. determining, with a precision having a covariance of less than about 10%, the activity $A_x$ of said polymerase in said test specimen corresponding to the rate of fluorometric signal generated by the binding of said dye to the double-stranded DNA formed by the action of said test specimen polymerase, said polymerase activity $A_x$ being determined as follows:

1) generating polymerase rates of reaction from the fluorometric signals generated over time for each of a series of samples containing DNA polymerase having known activities, $A_1, A_2, \ldots A_i \ldots A_n$, of Thermus aquaticus wherein n is the number of samples evaluated and is an integer of from 2 to 5, and generating the polymerase rate of reaction from the fluorometric signal generated over time from said test specimen, 2) determining a calibration using said rates of step 1) and said known polymerase activities $A_i$, and 3) predicting $A_x$ using said calibration of step 2) and said polymerase reaction rate of said test specimen.

16. The method of claim 15 wherein said bibenzimidazole dye is 2-[2-(4-hydroxyphenyl)-6-benzimidazole]-6-(1-methyl-4-piperazyl)benzimidazole trihydrochloride.

17. A test kit useful for the determination of a DNA polymerase, comprising:
   a. a single-stranded phage DNA as a template,
   b. the four deoxyribonucleosides, dATP, dCTP, dGTP and dTTP,
   c. a source of a metal ion DNA polymerase cofactor,
   d. a DNA primer complementary to said DNA template suitable for forming a double-stranded DNA therefrom, and
   e. a colorimetric or fluorescent dye which, when bound to said double-stranded DNA molecule formed from said template, exhibits a detectable signal, as opposed to when said dye is bound to said template.

18. The test kit of claim 17 comprising a source of magnesium or manganese ion as cofactor.

19. The test kit of claim 17 wherein said dye is a fluorescent dye selected from the group consisting of bibenzimidazole, ethidium, methidium and acridine dyes.

20. The test kit of claim 19 wherein said fluorescent dye is a bibenzimidazole dye.

21. The test kit of claim 19 wherein said fluorescent dye is selected from the group consisting of 2-[2-(4-hydroxyphenyl)-6-benzimidazole]-6-(1-methyl-4-piperazyl)benzimidazole trihydrochloride, acridine orange, methidium bromide, propidium iodide, ethidium bromide and 4',6'-diamidino-2-phenylindole.

22. The test kit of claim 17 wherein said phage DNA is M 13 phage DNA.

* * * * *